United States Patent [19]

Lipov

[11] Patent Number: 4,862,523
[45] Date of Patent: Sep. 5, 1989

[54] BUTTOCK AND LEG SUPPORT

[76] Inventor: Sergei Lipov, 2320 Central, Evanston, Ill. 60201

[21] Appl. No.: 142,028
[22] Filed: Jan. 11, 1988
[51] Int. Cl.⁴ ............................................. A41B 11/04
[52] U.S. Cl. ................................. 2/409; 128/80 R; 450/151
[58] Field of Search ............... 128/132 R, 80, 80 C, 128/165, 168, 169, 171; 2/409, 78 C, 239, 401, 22; 450/151, 100, 101, 107, 115, 122, 130, 156

[56] References Cited

U.S. PATENT DOCUMENTS

| | | | |
|---|---|---|---|
| 819,975 | 5/1906 | Bracco, Sr. | 450/101 |
| 963,878 | 7/1910 | Diver | 2/239 |
| 3,245,409 | 4/1966 | Martin | 450/107 X |
| 3,421,516 | 1/1969 | Erteszek | 450/100 |
| 4,089,064 | 5/1978 | Chandler, Jr. | 128/80 C X |
| 4,216,547 | 8/1980 | Picchione | 2/22 |
| 4,625,336 | 12/1986 | Derderian | 2/409 X |

Primary Examiner—Richard J. Apley
Assistant Examiner—H. Flaxman
Attorney, Agent, or Firm—Edward W. Osann, Jr.

[57] ABSTRACT

A waist band supported skin-tight garment incorporating an elastic support structure of counterwound elastic helices adapted to engage the lower extremities of the human body to counteract the effect of gravity on the soft tissues thereof to retard sagging of said tissues.

6 Claims, 1 Drawing Sheet

BUTTOCK AND LEG SUPPORT

BACKGROUND OF THE INVENTION

The present invention relates to a novel device designed to counteract the effect of gravity on the soft tissues in the lower extremities of the human body.

It is well known in the fields of anatomy and physiology that continued exposure to gravity causes a sagging effect on the soft tissues in the lower extremities of the body. By the term "soft tissues" is meant the various muscles of the buttocks, thighs and calves which tend to deflect downwardly under gravity when a person is standing or walking. The purpose of the present invention is to create a garment of daily use such as panty hose including means providing a force in opposition to the force of gravity, thereby counteracting or retarding the sagging of soft tissues in the body's lower extremities.

The prior art shows a number of devices utilizing straps of various types which engage upper and/or lower extremities for exercise or protection. The following patents exemplify such prior art:

| U.S. Pat. No. | Patentee | U.S. Pat. No. | Patentee |
|---|---|---|---|
| 968,878 | Diver | 4,089,064 | Chandler |
| 1,548,711 | Cooper | 4,216,547 | Picchione |
| 2,097,376 | Marshman | 4,424,596 | Jackson |
| 3,295,517 | Stevens | 4,625,336 | Derderian |
| 4,065,814 | Fox | | |

The present invention distinguishes over all of the foregoing patents in that it is constructed to perform an entirely different function which will be described below.

SUMMARY OF THE INVENTION

The general object of the present invention is to provide a device in the form of a novel garment which will engage the lower extremities of the human body to counteract the effect of gravity on the soft tissues so as to retard sagging.

Another object of the invention is to provide a garment of the character set forth above which will be anchored at the waist to maintain upward tension on the soft tissues of the buttocks and the legs.

A further object of the invention is to provide a garment of the foregoing nature wherein the upward thrust on the soft tissues will be maintained by counterwound helices.

Still another object is to provide a garment of the above type wherein the upward thrust on the soft tissues will be applied by means of elastic material built into the garment, the latter being attached at the waist only.

Other objects and advantages will become apparent as the following description proceeds, taken with the accompanying drawings.

While the present invention is susceptible of various modifications and alternative constructions, there is no intention to limit the invention to the specific forms illustrated and described herein. On the contrary, the intention is to cover all modifications and alternative constructions falling within the spirit and scope of the invention as set forth in the appended claims.

DETAILED DESCRIPTION OF THE INVENTION

Figure 1:
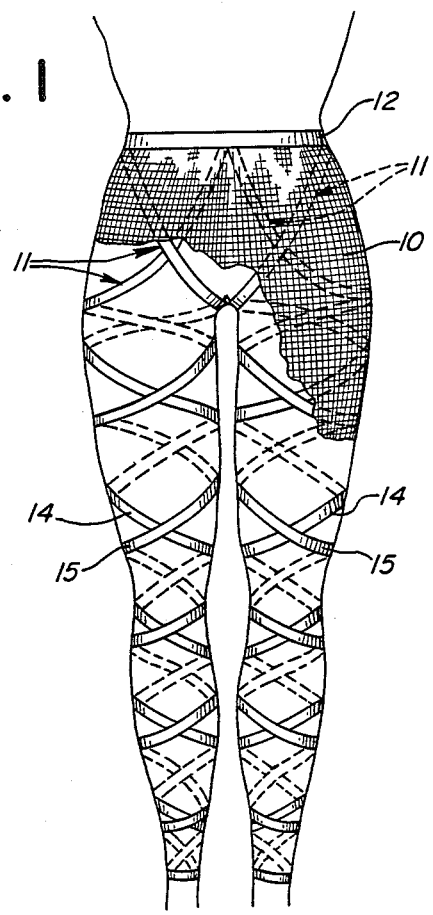
FIG. 1 is a rear view of an adult person wearing a buttock and leg support garment exemplifying the present invention.
Figure 2:
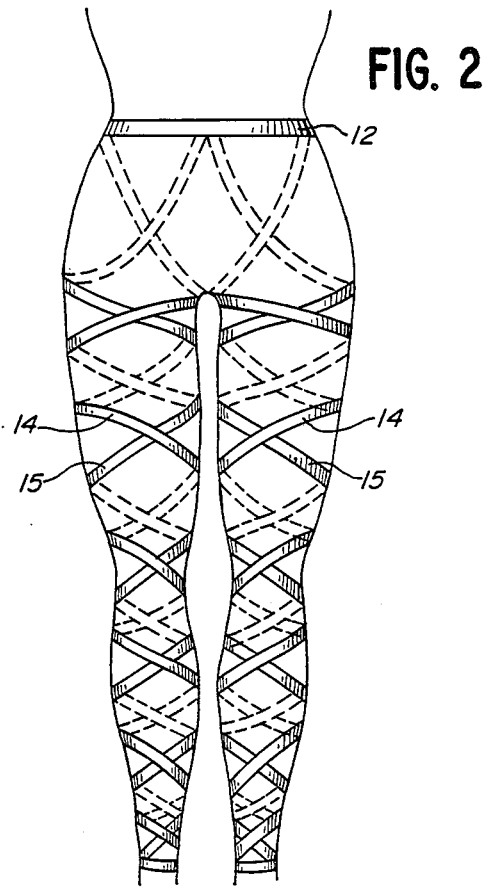
FIG. 2 is a front view of the person wearing the buttock and leg support garment shown in FIG. 1.

Referring more specifically to FIGS. 1 and 2, the present invention is there exemplified in a novel garment 10 of daily use such as panty hose, including a built-in uplift means 11. The latter provides an uplift force on the soft tissues of the lower extremeties in opposition to the force of gravity.

The uplift means 11 comprises a supporting waist band 12 connected to two or more counterwound elastic helices 14, 15, all attached to the inside face of the garment 10. The helices 14, 15 extend from the waist band 12, across the lower abdomen, across the buttocks, and down each leg. The helices may terminate anywhere above or below the knee, depending upon which area of the leg needs uplift support. Each helice may be defined by two separate elastic bands counterwound on the leg, or by a single elastic band wound from the waist band 12 to the termination point and backup the leg to the waist band 12. In the preferred form of the invention, and in order to maximize the uplift force, the garment 10 would not be attached at the bottom of the leg.

Figure 3:
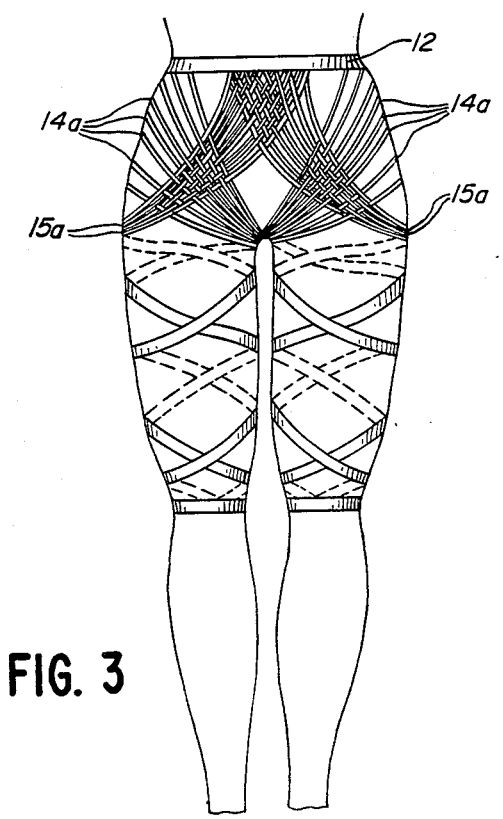
FIG. 3 is a rear view to FIG. 1 but illustrating the garment including counterwound helices terminating above the knee.

Turning next to FIG. 3, a modified form of the invention is there shown wherein the helices 14, 15 each include a greatly increased number of elastic bands 14a, 15a in the buttocks area of the garment 10. This construction provides more uniform distribution of the supporting force. It also hides or limits indentation into the soft tissues of the buttock and avoids a mark analogous to a panty line. In this instance, the counterwound helices 14, 15 are shown as terminating just above the knee. They could also in some instances, terminate between the ankle and the knee.

Figure 4:
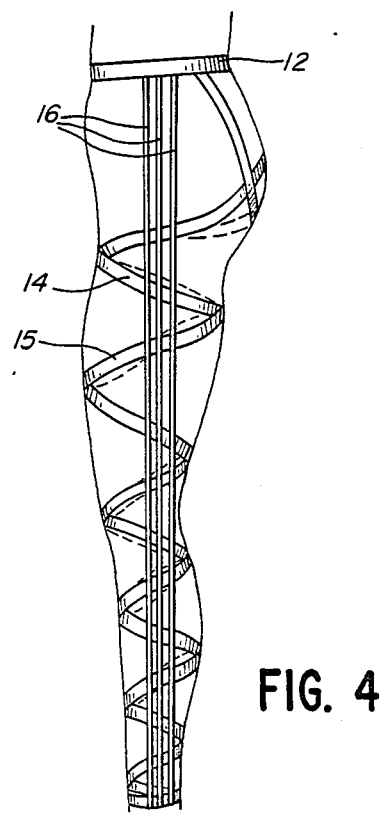
FIG. 4 is a side elevational view of the person shown in FIG. 3 illustrating the addition to the garment of straight elastic bands extending generally vertically along the sides of the lower extremities and in this instance terminating below the knee.

Referring to FIG. 4, another modified form of the invention is there shown. In this instance additional reinforcement of the garment 10 is provided by including a plurality of straight elastic bands 16 extending down the sides of the legs from the waist band 12 to the termination point on the legs. This point may be above or below the knee.

I claim as my invention:

1. A skin-tight garment of daily use such as panty hose incorporating a support structure consisting of elastic support helices and adapted to counteract the effect of gravity on the lower extremities of a human being, said garment comprising, in combination:
   (a) a body of fabric or other flexible sheet material;
   (b) a supporting waist band attached to said fabric body and adapted to encircle the wearer's waist line snugly;
   (c) a first pair of counterwound elastic support helices attached to and supported entirely from said waist band, said support helices extending downward along one leg to a dependent terminal point on the lower leg between the knee and the ankle, said counterwound elastic helices being attached to said garment along their length and exerting upward support on said lower extremities from said dependent terminal point to said waist band;

(d) a second pair of counterwound elastic support helices attached to and supported entirely from said waist band, said support helices extending downward along the other leg to a dependent terminal point on the lower leg between the knee and the ankle, said counterwound elastic helices being attached to said garment along their length and exerting upward support on said lower extremitites from said dependent terminal point to said waist band; and (e) each said pair of counterwound elastic support helices consisting of elastic and structure limiting the number of helical turns to support the claimed function.

2. A garment as set forth in claim 1, wherein said counterwound elastic helices terminate above the knee.

3. A garment as set forth in claim 1, wherein a plurality of straight elastic bands are connected to and supported from each side of said waist band and extend respectively down the leg so as to terminate between the knee and a dependent point above the ankle.

4. A skin-tight garment as set forth in claim 1, wherein said helices include a multiplicity of individual elastic strands affording uplift support for the buttocks.

5. A garment as set forth in claim 3, wherein said straight elastic bands terminate between the lower end of the thigh and the upper part of the knee.

6. A garment as set forth in claim 3, wherein disregard said helical elastic bands and said straight elastic bands terminate between the lower end of the thigh and the upper part of the knee.

* * * * *